United States Patent [19]

Novak

[11] 4,414,414

[45] Nov. 8, 1983

[54] 4,4'-DITHIODIANIL

[75] Inventor: Thaddeus J. Novak, Bel Air, Md.

[73] Assignee: The United States of America as represented by the Secretary of the Army, Washington, D.C.

[21] Appl. No.: 301,507

[22] Filed: Sep. 14, 1981

[51] Int. Cl.$^3$ .......................................... C07C 149/42
[52] U.S. Cl. ................... 564/271; 564/154; 564/272; 564/273; 564/274; 564/275; 564/276; 542/423; 562/432; 260/465 E; 260/510; 436/120
[58] Field of Search ......................................... 564/271

[56] References Cited

PUBLICATIONS

Novak, Thaddeus J., *Analytical Chemistry*, (1980), pp. 1851–1855.

Pohloudek-Fabini, R. et al., *Archiv der Pharmazie*, vol. 298, (1965), pp. 423–434.

*Primary Examiner*—Natalie Trousof
*Assistant Examiner*—L. Hendriksen
*Attorney, Agent, or Firm*—Robert P. Gibson; Anthony T. Lane; A. Victor Erkkila

[57] ABSTRACT

Novel 4,4'-dithiodianil compounds are prepared by reacting 4,4'-dithiodianiline with an aromatic or pyridine aldehyde, such as 4-nitrobenzaldehyde. The novel dithiodianil compounds can be employed for detecting thiol compounds. They react with thiols to yield reaction products which possess a different color from the novel dithiodianil compound itself. The color change obtained in this manner with the novel compounds in many cases is stronger than that obtained with Ellman's reagent frequently employed for detecting thiols.

1 Claim, No Drawings

4,4'-DITHIODIANIL

GOVERNMENT RIGHTS

The invention described herein may be manufactured, used and licensed by the Government for Government purposes without the payment to us of any royalty thereon.

BACKGROUND OF THE INVENTION

Numerous methods are known for detecting and estimating thiols, i.e. compounds containing a mercapto or sulfhydryl group —SH. A particularly valuable and frequently cited method is that described by G. H. Ellman, Arch. Biochem Biophys. 1959, 82, 70–77; also U.S. Pat. No. 3,119,668, which depends upon the formation of yellow colored 3-mercapto-6-nitrobenzoic acid anion by a displacement reaction between a thiol and 3,3'-dithiobis [6-nitrobenzoic acid] (Ellman's reagent). The detection test is extremely sensitive and the reaction with many thiols is very rapid. The method is particularly suited for many instrumental thiol analyses because of the great difference between the molar absorptivities of the reagent and its anion. However, the method is less useful for detection tests which depend on visual observation of a color change, since both Ellman's reagent and the displaced anion (the colored reaction product) are yellow to orange in color. Consequently, it is difficult to interpret data based on a color change in the same hue, particularly when the color change is very small, which is the case when the thiol is present in very low concentrations.

An objective of the present invention is to provide a novel class of compounds, which are suitable for the detection of thiols and in many cases avoid the aforesaid difficulties.

SUMMARY OF THE INVENTION

The present invention provides a novel class of dithiodianil compounds which can be advantageously employed for detecting thiols. The novel compounds possess the following general formula:

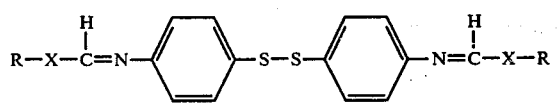

wherein R is an aryl or a pyridyl radical, which is unsubstituted or substituted by alkyl, alkoxy, halogen (chlorine, bromine, fluorine and iodine), nitro, cyano, hydroxy, carboxy, sulfo, dialkylamino, acylamino or quaternary ammonium and X is a direct bond or —CH=CH—. Preferred compounds of the foregoing formula are those wherein R is a phenyl radical which contains 0, 1, 2 or 3 substituents of the aforesaid type. Especially preferred compounds are those wherein R is

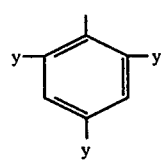

wherein y is hydrogen or an electronegative substituent of the group consisting of $NO_2$, and CN and halogen, at least one y being such an electronegative substituent.

The compounds of the foregoing formula can be prepared by reacting 4,4'-dithiodianiline of the formula

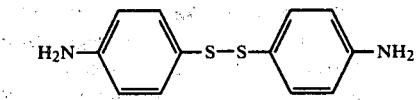

with an aldehyde of the formula

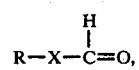

wherein R and X are defined as above, under conditions well known in the art for the preparation of Schiff's bases by reaction of aldehydes with primary amines. For example, the 4,4'-dithiodianiline can be mixed and reacted with about two molecular proportions of the aldehyde or a mixture of such aldehydes, in the presence of an inert organic solvent, such as methanol, ethanol and benzene, preferably at elevated temperatures up to 100° C., or higher. The reaction product can be separated from the reaction mixture in conventional manner, e.g. by cooling to precipitate the product from solution or by removal of the solvent by distillation. The resulting product can be purified by recrystallization from a suitable solvent.

The following are illustrative of aldehydes which can be reacted with 4,4'-dithiodianiline to produce the novel dithiodianil compounds of the aforesaid formula:

benzaldehyde
  2-chlorobenzaldehyde
  2-bromobenzaldehyde
  3-chlorobenzaldehyde
  3-bromobenzaldehyde
  4-chlorobenzaldehyde
  4-bromobenzaldehyde
  4-fluorobenzaldehyde
  2,4-dichlorobenzaldehyde
  4-cyanobenzaldehyde
  2,4,6-trichlorobenzaldehyde
  4-methylbenzaldehyde
  4-carboxybenzaldehyde (4-formylbenzoic acid)
  4-sulfobenzaldehyde (4-formylbenzenesulfonic acid)
  4-methoxybenzaldehyde
  4-hydroxybenzaldehyde
  3-hydroxy-4-nitrobenzaldehyde
  2-nitrobenzaldehyde
  3-nitrobenzaldehyde
  4-hydroxy-5-iodo-3-methoxybenzaldehyde
  4-isopropylbenzaldehyde
  4-acetamidobenzaldehyde
  3,4-diethoxybenzaldehyde
  4-dimethylaminobenzaldehyde
  4-dimethylaminocinnamaldehyde
  4-nitrobenzaldehyde
  2,4-dinitrobenzaldehyde
  2,6-dinitrobenzaldehyde
  4-nitrocinnamaldehyde
  4-cyanobenzaldehyde
  1-naphthaldehyde
  2-formylpyridine (2-pyridinecarboxaldehyde)

4-formylpyridine (4-pyridinecarboxaldehyde)
2-formyl-1-methylpyridinium chloride
4-formyl-1-methylpyridinium chloride The novel dithiodianil compounds can be employed for testing a substance for the presence of a mercapto group therein by contacting the substance with one or more of the novel compounds. If the substance contains a mercapto group, a reaction takes place between the dithiodianil compound and the mercapto group, forming a reaction product (a thiolate anion), which possesses a different color than the dithiodianil compound and in many cases provides a greater color change than is obtained with Ellman's reagent. For this purpose the novel compounds may be employed in a manner similar to methods used with Ellman's reagent, e.g. dissolved in a suitable solvent or dispersed in or on a finely divided solid substance, e.g. silica or alumina gel, paper, cloth, etc. Dithiodianil compounds of the present invention are soluble in water and aqueous media when they contain a quaternary ammonium salt or a carboxy or sulfo group in the form of a sodium or other water soluble salt.

The following examples illustrate and describe the process of making and using the invention.

EXAMPLE 1

A solution obtained by dissolving 4,4'-dithiodianiline (10 g. = 0.04 mol) in hot methanol (300 ml) and purified by filtration through a bed of decolorizing carbon, was mixed with a solution obtained by dissolving 4-nitrobenzaldehyde (0.10 mol) in hot methanol (250 ml). The hot mixture was then refluxed for 15 minutes, causing the reaction product to precipitate. The reaction mixture was cooled to ambient temperature and filtered. The product was purified by dissolving it in 2.5 times its weight of hot dimethylformamide (DMF) and cooling the solution to room temperature to crystalize the product. The crystalline product thus obtained was separated by filtration, washed with methanol and air dried. The N,N'-bis (4-nitrobenzylidene)-4,4'-dithiodianiline product possessed a melting point of 198°–201° C. and was obtained in 81% theory yield.

In similar manner, by employing the procedure described in the foregoing example but using one of the aldehydes shown in Table 1 in place of 4-nitrobenzaldehyde, the corresponding 4,4'-dithiodianiline derivatives were obtained. The yields varied from 80% to 100% of theory.

TABLE 1

| Example | Aldehyde | mp °C. (uncorrected) of 4,4'-dithiodianil compound formed |
|---|---|---|
| 1 | 4-nitrobenzaldehyde | 198–201 |
| 2 | 4-nitrocinnamaldehyde | 177–179 |
| 3 | 3-nitrobenzaldehyde | 104–105 |
| 4 | 2-nitrobenzaldehyde | 135–137 |
| 5 | 2,4-dinitrobenzaldehyde | 190–191 |
| 6 | 4-cyanobenzaldehyde | 215–217 |
| 7 | 4-fluorobenzaldehyde | 119–121 |
| 8 | benzaldehyde | not determined |
| 9 | 4-hydroxybenzaldehyde | " |
| 10 | 4-carboxybenzaldehyde | " |
| 11 | 3-hydroxy-4-nitrobenzaldehyde | " |
| 12 | 2,6-dinitrobenzaldehyde | " |
| 13 | 4-formyl-1-methylpyridinium iodide | " |

Notes:
(a) The products of examples 8-12 were not purified.
(b) The product of example 13 was not recovered from the methanol solution in which the reaction was carried out, but was employed directly for Thiol detection tests as described below.
(c) The products of examples 3 and 4 separated from the reaction mixture as liquids. These reaction mixtures were stirred overnight at room temperature to crystalize the products.
(d) In the purification of the products of examples 3, 5 and 7, since crystallization did not occur immediately after cooling the dimethylformamide solution to room temperature, methanol was added to precipitate the products.

The dithiodianil compounds of examples 1–13 were tested in the following manner to determine the color changes produced on contact with thiols by spot detection tests.

Into each cavity of a white ceramic spot plate was placed one 30 microliter drop of a DMF solution containing 0.5% of pH 8 potassium dihydrogen phosphate-sodium hydroxide buffer (0.05 M) and 0.001 M of the dithiodianil compound. To each of the above drops was added a 30 microliter drop of a solution in DMF of the thiol to be tested, the concentration of the thiol in the 30 microliter drop decreasing until a color change was no longer visible. The results are set forth in Table 2. The detection limits varied from 0.5 to 2 micrograms with 1-butanethiol, from 2 to 5 micrograms with 2-naphthalenethiol, and from 10 micrograms to more than 100 micrograms with thiocholine iodide. The results show that although Ellman's reagent produced a reaction product (color) having in some cases better stability, under the spot test conditions several of the novel dithiodianil compounds—specifically those of examples 1, 2, 4, 5, 6, 12 and 13 produced more striking color changes and all gave more sensitive tests with 1-butanethiol.

TABLE 2

| Compound Example | Detection Limit,[b,c] microgram(min) | | | Color Observed | |
|---|---|---|---|---|---|
| | NT | TCI | BT | Initial Color | Final Color |
| 1 | 2(1) | 10(2) | 1(1.5) | yellow | greenish blue-green |
| 2 | 2(2.5) | 10(1) | 0.5(2) | pale yellow | greenish blue-green |
| 3 | 2(1.5) | 10(0.5) | 1(1) | colorless | orange |
| 4 | 2(1) | 10(1) | 1(1) | yellow | red |
| 5 | 5(10) | 10(.5) | 1(2) | yellow | green |
| 6 | 2(2) | 10(2.5) | 0.5(1) | pale yellow | red |
| 7 | 5(2) | 100(d) | 2(1) | colorless | yellow-greenish yellow |
| 8[e] | — | — | — | yellow | orange |
| 9[e] | — | — | — | yellow | yellow orange |
| 10[e] | — | — | — | yellow | orange |
| 11[e] | — | — | — | yellow | greenish yellow |
| 12[e] | — | — | — | yellow | greenish blue-green |
| 13[e] | — | — | — | yellow | greenish blue-green |
| Ellman's | 2(1) | 5(1) | 10(5) | yellow | orange |

TABLE 2-continued

| Compound Example | Detection Limit,[b,c] microgram(min) | | | Color Observed | |
|---|---|---|---|---|---|
| | NT | TCI | BT | Initial Color | Final Color |
| reagent | | | | | |

[a]Tests were carried out at 25 ± 1° C. with illumination (430 1×) from artificial fluorescent lights.
[b]Code refers to the following thiols: NT, 2-naphthalenethiol; TCI, thiocholine iodide; BT, 1-butanethiol.
[c]Values in parentheses are the times of return to the original color of the detector solution after maximum color had been reached using the indicated level of thiol. The detector reagent was observed for a positive test immediately after addition of the solutions of 2-naphthalenethiol or thiocholine iodide and 1 min after addition of solutions of 1-butanethiol.
[d]Color fades within a few seconds after addition of the thiocholine iodide solution.
[e]The dithiodianil compounds of examples 8–12 were not purified and the compound of example 13 was not isolated from methanol reaction mixture. Instead, these compounds in crude form or in the methanol solution were added to the buffered DMF solvent.

EXAMPLE 14

Test papers were made by preparing a 0.001 M solution of the dithiodianil compound of example 2 in DMF containing 0.5% of pH 8 potassium dihydrogen phosphate-sodium hydroxide buffer (0.05 M) and applying the solution to paper discs made of Whatman DE-81 ion exchange paper composed of diethylaminoethylcellulose. The test papers were exposed to 1-butanethiol vapors at a concentration of 6–7 micrograms of 1-butanethiol per liter of air for a 10 minute exposure period. Test papers thus exposed gave a visible color change from yellow (initial) to brownish red (final).

Similar color changes from yellow to brownish-red were obtained when the dithiodianil compounds of examples 1 and 4 were employed in place of the compound of example 2.

When the foregoing procedure was repeated by using Ellman's reagent in place of the compound of example 2, the color changed from yellow to orange. This slight color change in the same hue was difficult to interpret and hence was considered unsatisfactory.

The U.S. Army utilizes a standard Detector Kit, Chemical Agent M256 for detecting the presence of toxic chemical agents, such as hydrogen cyanide gas. There is a need for a training device, which can be employed during integrated field training excercises to detect the presence of medically approved simulant agents, notably 1-butanethiol, as well as to familiarize personnel with the proper use of the M-256 Kit. For this purpose the training device must duplicate the M-256 Kit in physical configuration, operation and color response. By employing the standard M256 Kit containing a test paper prepared as described in example 14, the M256 Kit can be employed as a training device, since the color change obtained on contact of the paper with vapors of the chemical simulant 1-butanethiol is closely similar to the color change obtained when the standard M256 Kit is contacted with hydrogen cyanide gas.

The color change produced by the reaction of the novel dithiodianil compounds with thiols is influenced by the polarity of the solvent and the support material used. Thus, for example, in the following solvent series, the wave length of maximum absorption of a buffered alkaline solvent solution of the reaction product of the dithiodianil compound of example 2 with 1-butanethiol decreases from tetrahydrofuran (longest) to methanol (shortest), the wavelength of maximum absorption of the solution of the reaction product being substantially longer than that of the solution of the dithiodianil compound per se in the same solvent:

Solvent
tetrahydrofuran
N,N-dimethylacetamide
1-methyl-2-pyrrolidinone
pyridine
N,N-dimethylformamide
dimethyl sulfoxide
ethyl ether
benzonitrile
nitrobenzene
acetone
benzene
propanediol 1,2-carbonate
acetonitrile
nitromethane
n-butanol
ethanol
formamide
methanol It is further illustrated by the fact that when the dianil compound of example 2 is reacted with 1-butanethiol in DMF solution, the color changes from yellow to greenish blue, whereas the same reagent solution changes from yellow to red-violet when the reaction is performed on a support material of Whatman DE-81 paper, as described in example 14. The strongest color changes (responses) to 1-butanethiol are obtained with the novel dithiodianil compounds when the solvent contains a small amount, e.g. 0.5% of an aqueous buffer in the 8–12 pH range. The strength of the color change is independent of the type of aqueous buffer used. Dimethylformamide and dimethylsulfoxide are the preferred solvents because they combine high test sensitivity with stability of test solutions. Expecially sensitive responses are obtained by employing Whatman DE-81 ion exchange paper composed of diethylaminoethylcellulose as the support matrix.

The foregoing disclosure is merely illustrative of the principles of this invention and is not to be interpreted in a limiting sense. We wish it to be understood that we do not desire to be limited to the exact details of construction shown and described because obvious modifications will occur to a person skilled in the art.

We claim:
1. The 4,4'-dithiodianil compound of the formula:

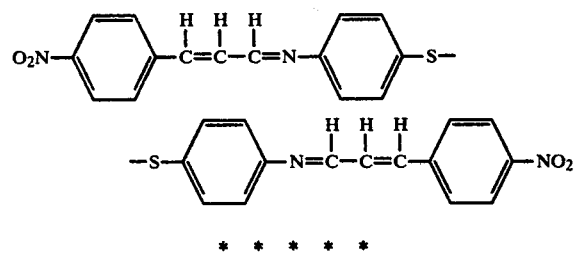

* * * * *